US008428315B2

(12) United States Patent
Suetens et al.

(10) Patent No.: US 8,428,315 B2
(45) Date of Patent: Apr. 23, 2013

(54) METHOD AND SYSTEM FOR PRE-OPERATIVE PREDICTION

(75) Inventors: Kevin Suetens, Bonheiden (BE); Paul Suetens, Bonheiden (BE); Wouter Mollemans, Leest (BE); Filip Schutyser, Sint-niklaas (BE); Dirk Loeckx, Leuven (BE); Vincent Masselus, Heverlee (BE); Philip Dutre, Leuven (BE)

(73) Assignee: Medicim N.V., Mechelen (BE)

( * ) Notice: Subject to any disclaimer, the term of this patent is extended or adjusted under 35 U.S.C. 154(b) by 1326 days.

(21) Appl. No.: 11/868,313

(22) Filed: Oct. 5, 2007

(65) Prior Publication Data

US 2008/0159608 A1 Jul. 3, 2008

Related U.S. Application Data

(63) Continuation of application No. PCT/BE2006/000035, filed on Apr. 7, 2006.

(30) Foreign Application Priority Data

Apr. 8, 2005 (GB) .................................. 0507204.6

(51) Int. Cl.
*G06K 9/00* (2006.01)
(52) U.S. Cl.
USPC ........................................................ 382/128
(58) Field of Classification Search .................. 382/128, 382/129, 130, 131, 132, 154; 345/420, 425, 345/430; 264/222
See application file for complete search history.

(56) References Cited

U.S. PATENT DOCUMENTS

| 6,081,273 | A | * | 6/2000 | Weng et al. | 345/420 |
| 6,645,413 | B2 | * | 11/2003 | Jacobs | 264/222 |
| 2002/0118890 | A1 | * | 8/2002 | Rondinelli | 382/276 |
| 2005/0148859 | A1 | * | 7/2005 | Miga et al. | 600/410 |
| 2005/0280644 | A1 | | 12/2005 | Ikezawa | |
| 2006/0161052 | A1 | * | 7/2006 | Colombet et al. | 600/300 |
| 2006/0280342 | A1 | * | 12/2006 | Lee et al. | 382/118 |
| 2008/0247622 | A1 | * | 10/2008 | Aylward et al. | 382/131 |

FOREIGN PATENT DOCUMENTS

| EP | 1355277 A2 | 10/2003 |
| EP | 1355277 A3 | 1/2004 |

OTHER PUBLICATIONS

Xia et al. ("Three-Dimensional Virtual-Reality Surgical Planning and Soft-Tissue Prediction for Orthgnathic Surgery", IEEE Transaction on Information Technology in Biomedicine, vol. 5, No. 2, Jun. 2001, pp. 97-107).*

(Continued)

*Primary Examiner* — Amara Abdi
(74) *Attorney, Agent, or Firm* — Knobbe, Martens, Olson & Bear LLP

(57) ABSTRACT

A system and method for pre-operatively obtaining a prediction of a post-operative image of at least part of a body is disclosed. A 3D pre-operative description is determined of at least part of a body, and a pre-operative 2D photograph is acquired of the at least part of the body from any viewing position. The 3D pre-operative description is matched with the pre-operative 2D photograph, and a deformation field is determined for deforming the 3D pre-operative description. A predicted post-operative image of a 3D post-operative description of the at least part of the body is derived by means of the deformation field and the pre-operative 2D photograph.

24 Claims, 20 Drawing Sheets

OTHER PUBLICATIONS

Barre, S., et al., "Three-dimensional visualization system as an aid for facial surgical planning", Proceedings of the SPIE—The International Society for Optical Engineering SPIE-INTL Soc. Opt. Eng USA, vol. 4319, 2001, pp. 252-263, XP002389572, TSSN: 0277-786X.*

Xia et al (Computer-assisted three-dimensional surgical planning and simulation, 3D soft tissue planning and prediction. Int. J. Oral Maxillofoc. Surg. 2000, 29: 250-258. © Munksgaard, 2000).*

Xia, J., et al., "Three-dimensional virtual reality surgical planning and simulation workbench for orthognathic surgery", International Journal of Adult Orthodontics and Orthognatic Surgery, Quintessence Publishing, Carol Stream, IL, US, vol. 15, No. 4, Dec. 21, 2000, pp. 265-282, XP008032679, ISSN: 0742-1931.

Barre, S., et al., "Three-dimensional visualization system as an aid for facial surgical planning", Proceedings of the Spie—The International Society for Optical Engineering Spie-Int. Soc. Opt. Eng USA, vol. 4319, 2001, pp. 252-263, XP002389572, ISSN: 0277-786X.

Yip, B., et al., "An effective eye gaze correction operation for video conference using antirotation formulas", ICICS-PCM 2003, Proceedings of the 2003 Joint Conference of the Fourth International Conference on Information, Communications and Signal Processing and Fourth Pacific-Rim Conference on Multimedia (IEEE Cat. No. 03EX758) IEEE Piscataway, NJ, USA, vol. 2, 2003, pp. 699-703, vol. 2, XP010701216, ISBN: 0-7803-8185-8.

International Search Report, Application No. PCT/BE2006/000035, Date of mailing: Aug. 22, 2006, 4 pages.

Iwakiri, Yuya, et al., "Fast Texture Mapping of Photographs on a 3D Facial Model"; Proc Image and Vision Computing NZ, pp. 390-395; Palmerston North, New Zealand, Nov. 2003.

Mollemans, Wouter, et al.; "Very fast soft tissue predictions with mass tensor model for maxillofacial surgery planning systems", Proc Computer Assisted Radiology and Surgery (CARS); International Congress Series 1281 (2005); pp. 491-496; www.ics-elsevier.com.

Pighin, Frédéric, et al.; "Modeling and Animating Realistic Faces from Images", Int J Comp Vision 50 (2); pp. 143-169, 2002.

Xia, James, et al.; "Computer-assisted three-dimensional surgical planning and simulation: 3D color facial model generation"; International Journal of Oral & Maxillofacial Surgery, 2000; 29: 2-10.

Xia, James, et al.; "Computer-assisted three-dimensional surgical planning and simulation: 3D soft tissue planning and prediction"; International Journal of Oral & Maxillofacial Surgery, 2000; 29: 250-258.

* cited by examiner pre-operative state pre-operative state post-operative state post-operative state

METHOD AND SYSTEM FOR PRE-OPERATIVE PREDICTION

CROSS-REFERENCE TO RELATED APPLICATIONS

This is a continuation application under 35 U.S.C. §120 of WO 2006/105625 A1, filed as PCT/BE2006/000035 on Apr. 7, 2006, which is hereby incorporated by reference.

BACKGROUND OF THE INVENTION

1. Field of the Invention

The present invention relates to a method for the pre-operative prediction of a body or a part of a body, e.g., the face, after surgery. The invention also relates to a planning system wherein the method can be applied.

2. Description of the Related Technology

In maxillofacial and plastic surgery or dermosurgery parts of the body, such as the skull, dentition, soft tissues or skin patches, are surgically remodelled or restored. An example is orthognatic surgery, in which the relation of the jawbones is adjusted. Another example is breast augmentation, in which the breasts are enlarged using breasts implants.

Generating realistic images (e.g., of faces) has been a central goal in three-dimensional (3D) shape acquisition, animation and visualisation.

3D Acquisition

Several methods exist to acquire a 3D geometric description of (a part of the body. Well-known are the medical imaging modalities, such as CT and MRI, and 3D photographic systems. The latter can be subdivided into two categories, i.e., those using active methods, which project a specific pattern on the body, and those using passive methods, which acquire a 3D geometric description of the body from one or more images and illumination conditions, with or without the use of a priori geometric knowledge. Simultaneously with the 3D geometric description, 3D photographic systems deliver the texture of the body, which is used to render the 3D surface.

Animation

Several methods exist to animate a 3D body shape. Motion simulation can be based on heuristic rules, physics-based knowledge, or it can be image-derived (e.g., building a statistical deformation model based on a set of images from different persons and/or expressions). The result can be natural or artificial. For example, the facial motion of one person can be used to drive the facial motion of another person.

Visualisation 3D visualization or rendering uses a texture map and a reflectance model of the (part of the) body.

Texture mapping refers to a computer graphics technique wherein a texture image (or texture map) is applied to a polygonal mesh or some other surface representation by coupling the texture image (or texture map) (with associated colour/gray value) to the 3D surface. The result is that (some portion of) the texture image is mapped onto the surface when the surface is rendered.

Texture is derived from one or more 2D or 3D photographs of the body. When using a 3D photographic system, a texture map is typically delivered simultaneously with the 3D shape description.

when using 2D photographs, a method to match or register these 2D photographs with the 3D surface description is needed. Matching can be done based on a set of corresponding points, or on a metric (e.g., mutual information) that expresses the correspondence between 2D-image-derived features and 3D-shape-based properties.

The model of body reflectance can be based on skin or skin-like diffuse and specular (mirror-like reflection) properties.

2D visualization has been used to show (a part of) the body under simulated or artificial illumination conditions and for animation by morphing (part of) the body. In these applications, photo-realism is the primary concern.

The following documents relate to the subject-matter described herein.

'Computer-assisted three-dimensional surgical planning and simulation', J Xia et al, 3D color facial model generation, Int J Oral Maxillofac Surg, 29, pp, 2-10, 2000, 'Computer-assisted three-dimensional surgical planning and simulation: 3D soft tissue planning and prediction', Xia et al, Int J Oral Maxillofac Surg, 29, pp. 250-258, 2000, 'Three-dimensional virtual reality surgical planning and simulation workbench for orthognathic surgery', Xia et al, Int J Adult Orthod Orthognath Surg, 15(4), 2000, 'Three-dimensional virtual-reality surgical planning and soft-tissue prediction for orthognatic surgery', Xia et al., IEEE Information Technology in biomedicine 5(2), pp. 97-107, 2001, 'Fast Texture mapping of photographs on a 3D facial model', Iwakiri et al, Proc Image and Vision Computing New Zealand 2003, November 2003, Palmerston North, New Zealand, pp. 390-395.

The methods of Xia et al. and of Iwakiri et al. use a set of photographs comprising a frontal (0° view), right (90° view) and left (270° view) photograph of the patient, which are projected as a texture map onto the 3D head mesh obtained from CT for 3D visualization.

SUMMARY OF CERTAIN INVENTIVE ASPECTS

The system and method provides for pre-operatively simulating or predicting an accurate image of the patient's appearance after surgery, in particular maxillofacial or plastic surgery. A planning system is provided where the method can be applied.

In one embodiment, there is a method for pre-operatively obtaining a prediction of a post-operative image of at least part of a body, comprising determining a 3D pre-operative description of at least part of a body, acquiring a pre-operative 2D photograph of the at least part of the body from any viewing position, matching the 3D pre-operative description with the pre-operative 2D photograph, determining a deformation field for deforming the 3D pre-operative description, typically with a 3D planning system, and deriving by means of the deformation field and the pre-operative 2D photograph a predicted post-operative image of a 3D post-operative description of the at least part of the body.

In another embodiment, the predicted post-operative image is a 2D photograph obtained by deforming the pre-operative 2D photograph using said deformation field.

In another embodiment, the predicted post-operative image is a 3D image. In this case a plurality of pre-operative 2D photographs is acquired and subsequently used in later portions of the method.

The method further comprises generating from the 3D pre-operative description a 3D pre-operative surface mesh of at least the contours of the at least part of the body. Deriving the predicted image comprises deriving from the 3D pre-operative surface mesh a prediction of a 3D post-operative surface mesh of at least the contours of the at least part of the body. The prediction of the contours is then used in the determination of the deformation field.

In another embodiment, the 3D pre-operative description is obtained using a 3D image acquisition system. Such 3D image acquisition system can be a Computerised Tomography system, a Magnetic Resonance Imaging system or a 3D photographic system.

The matching is preferably performed by means of a set of corresponding points on said 3D pre-operative description and said 2D pre-operative photograph. Alternatively the matching is performed by means a metric expressing the correspondence between features derived from the pre-operative 2D photograph and properties based on the 3D pre-operative description.

In a more specific embodiment, the method further comprises taking a picture of a calibration object. The picture of the calibration object can then be used for calibrating the camera with which the pre-operative 2D photograph is acquired.

After the matching, a texture map for 3D visualization is created from the matched pre-operative 2D photographs.

The 3D pre-operative description comprises typically a soft tissue description of the at least part of the body. It also comprises information about the internal structure of the at least part of the body.

In another embodiment, there is a surgical planning system for pre-operatively showing a predicted post-operative image of at least part of a body, comprising means for determining a 3D pre-operative description of at least part of a body, means for matching the 3D pre-operative description with a 2D pre-operative photograph of the at least part of the body, calculation means for determining a deformation field to deform the 3D pre-operative description and for deriving a predicted post-operative image of a 3D post-operative description of the at least part of the body, and display means for showing the predicted post-operative image.

In a specific embodiment, the predicted post-operative image is a 3D image. Alternatively the predicted post-operative image is a predicted post-operative 2D photograph obtainable by deforming the pre-operative 2D photograph using the deformation field.

DETAILED DESCRIPTION OF CERTAIN INVENTIVE EMBODIMENTS

Figure 1A:
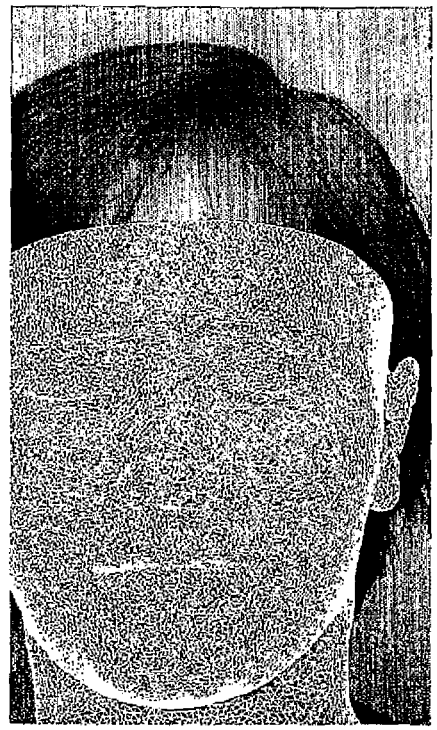
FIG. 1a represents a 3D pre-operative surface mesh, projected onto the 2D pre-operative photographs after registration.
Figure 1A:
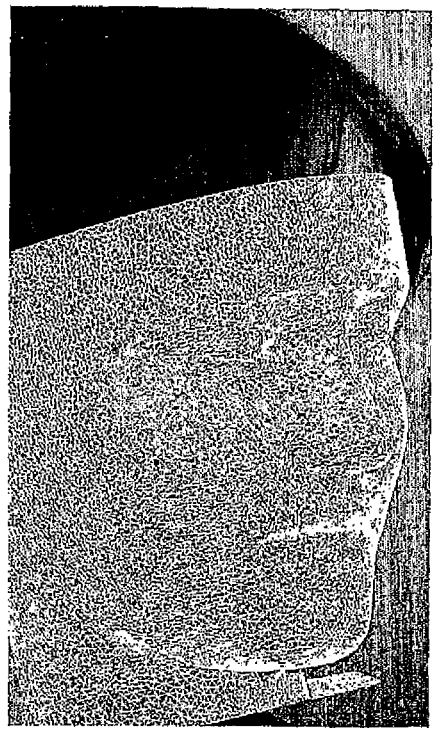
Figure 1A:
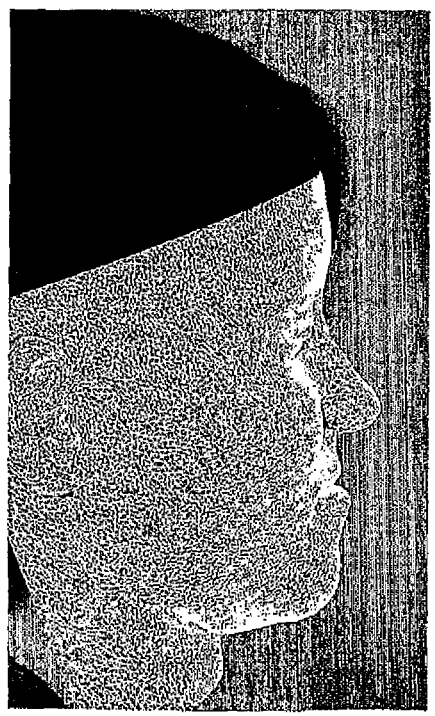

In the approach according to an inventive aspect one or more 2D photographs taken from any viewing position can be used. A viewing position is to be considered as a vector having a direction as well as a magnitude, e.g., a viewing position consists of a viewing direction and a camera distance. The number of 2D photographs is thus arbitrary. Furthermore the visualization is not restricted to 3D visualisation, for which the 2D photographs are used as texture maps, but a single arbitrary pre-operative 2D photograph can be deformed into a simulated post-operative 2D photograph using a physics-based reliable, personalised and accurately predicting 3D deformation field.

While 3D visualisation using texture mapping lacks photo-realism (e.g., unnatural texture blending and hair modelling artifacts (particularly when using medical imaging, such as CT for 3D image acquisition), the simulated post-operative 2D photograph has intrinsically the same photo-realism as the original pre-operative photograph.

The ability to show the patient's appearance can be integrated into a system for 3D pre-operative planning. In certain embodiments, by "planning system" is meant a software environment that allows a physician to plan or simulate the procedure of an intervention. It can for example be used to predict the outcome of that intervention, to try out different procedures, to optimise the procedure, to prepare it and to improve the communication between the medical staff and with the patient.

Real time 3D visualisation using texture mapping offers an added value to the surgeon while using the 3D planning system, e.g., when adjusting or repositioning bony structures or an implant. Accuracy and integration in the planning procedure are of primary importance, and photo-realism is of minor importance. Visualisation is possible from any viewing direction.

The 2D geometrically deformed photographs on the other hand offer both high accuracy and high photo-realism and are for example an excellent means to discuss the expected outcome of a surgical procedure with the patient. Although visualisation is restricted to the viewing directions of the original 2D photographs, the number as well as the viewing directions can be arbitrarily chosen.

Initially, a 3D pre-operative image is acquired of (a part of) a patient's body. A 3D image acquisition system is preferably used thereto, such as CT (Computerised Tomography), MRI (Magnetic Resonance Imaging) or any other 3D scanning or photographic system. 3D medical imaging modalities, such as CT or MRI, offer geometric information of the body contour (further also referred to as the 'soft tissue') and internal structures, such as the bony structures. Based on the volumetric data, the 3D contour of the skin and other tissues, such as bone, are segmented. In the case of skin and bone, segmentation can for example be performed by simple thresholding. Instead of a 3D medical imaging modality, any other 3D scanning device can be used to obtain the outer body contour, such as a 3D photographic system. 3D photographic systems can be subdivided into two categories, e.g., those using active methods, which project a specific pattern on the body, and those using passive methods, which acquire a 3D geometric description of the body from one or more images and illumination conditions, with or without the use of a priori geometric knowledge. In '*Modeling and animating realistic faces from images*' (Pighin et al., *Int J Comp Vision* 50(2), pp. 143-169, 2002) for example, a 3D generic face model is interactively fitted to a set of images to acquire the 3D shape.

Figure 1B:
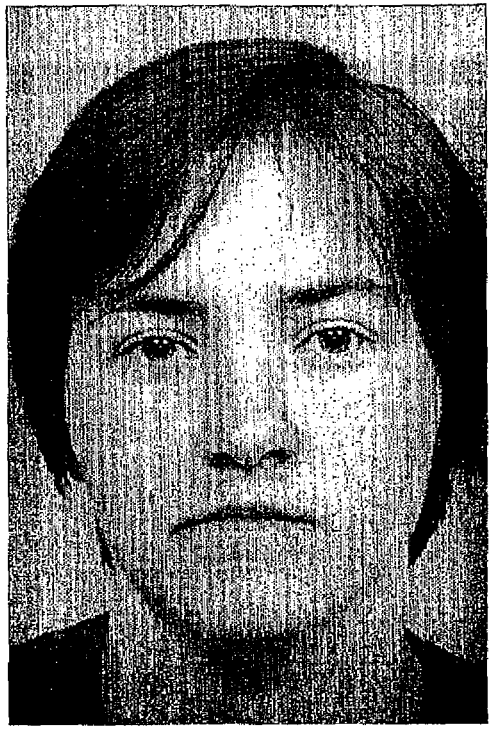
FIG. 1b and FIG. 1c show 2D pre-operative and post-operative photographs, respectively.
Figure 1B:
Figure 1B:
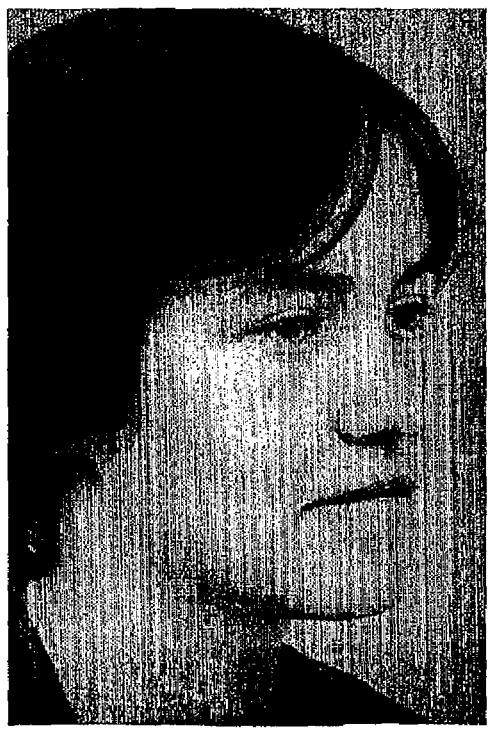
Figure 2A:
FIG. 2a represents a 3D pre-operative surface mesh, projected onto the 2D pre-operative photographs after registration.
Figure 2B:
FIG. 2b and FIG. 2c show 2D pre-operative and post-operative photographs, respectively.
Figure 3A:
FIG. 3a represents a 3D surface mesh, obtained with a 3D photographic system, projected onto the 2D photographs after registration.
Figure 3B:
FIG. 3b shows 2D photographs.
Figure 4:
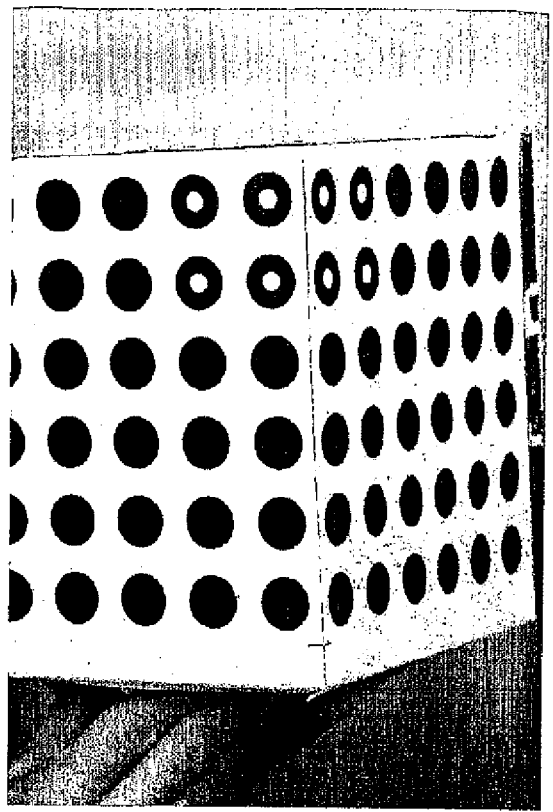
FIG. 4 represents a calibration object.

Next a set of (one or more) 2D photographs of (a part of) the body from any viewing direction and camera distance (e.g., any viewing position as previously defined) using any camera is acquired. As illustrated in FIGS. 1*b*, 2*b* and 3*b*, one or more 2D pictures are taken from arbitrarily chosen directions. To improve the accuracy of the registration method as described below, it is recommended to take a picture of a calibration object (FIG. 4) to calculate the internal parameters of the camera and to freeze these settings during the remainder of the photo session (see below).

The 3D data are used to generate a 3D surface mesh of the body contour (the 'soft tissue') and, if needed by the planning system, of other tissues such as bone. Surface meshes such as the triangular meshes shown in FIGS. 1*a*, 2*a* and 3*a*, can for example be created using the marching cubes algorithm.

Figure 5:
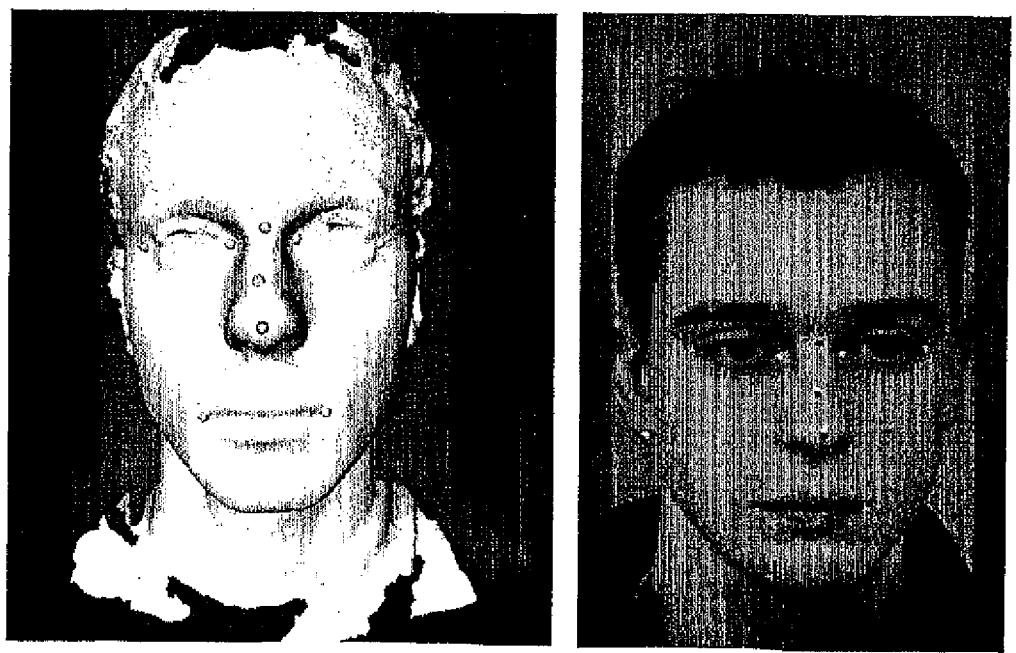
FIG. 5 represents on the left a set of points specified manually onto the 3D rendered untextured surface, obtained from the 3D surface mesh and on the right a set of (bright) points specified manually onto the 2D photograph, together with the above set of (dark) points obtained by matching the 3D surface with the 2D photograph.
Figure 7:
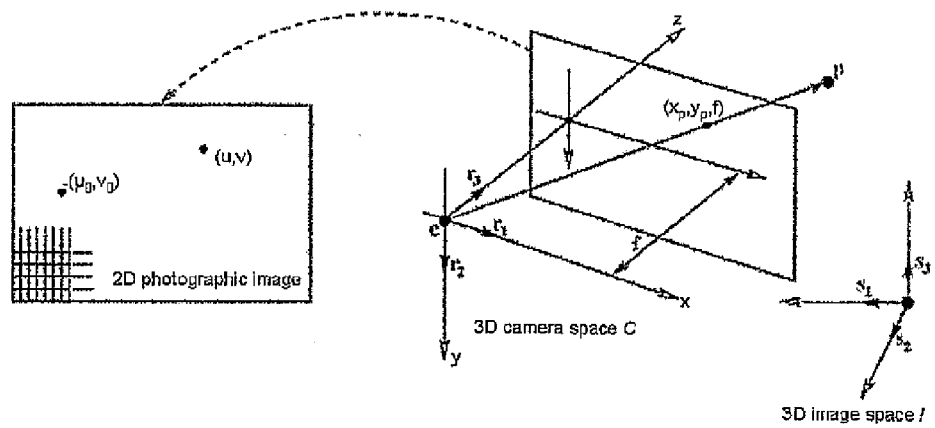
FIG. 7 gives a schematic representation of the 3D image space I, the 3D camera space C and the 2D photographic image.

A registration method is then applied to match or register the 3D pre-operative surface description with the 2D photographs. One way to align or register the 3D surface with a 2D photograph is shown in FIG. 5, where a set of corresponding points on the 3D surface and the 2D photograph, respectively, is used. The problem then is how to transfer a point from the 3D image space I to the related camera space C and further to the corresponding 2D photographic image. It is assumed that the camera can be modelled as a perspective pinhole camera with its optical centre located at c (see FIG. 7). The geometric relation between I and C can then be expressed by a rotation R and a translation I. Once the coordinates of a point p(x, y, z) in C are known, its projection ($x_p$, $y_p$, f) in the plane z=f can easily be calculated using the following equations (see FIG. 7):

$$\frac{x}{x_p} = \frac{z}{f} \quad \text{(eq. 1)}$$

$$\frac{y}{y_p} = \frac{z}{f}$$

This projection can be written in matrix form as follows:

$$\begin{bmatrix} x_p \\ y_p \\ 1 \end{bmatrix} \cong \begin{bmatrix} f & 0 & 0 \\ 0 & f & 0 \\ 0 & 0 & 1 \end{bmatrix} \begin{bmatrix} 1 & 0 & 0 & 0 \\ 0 & 1 & 0 & 0 \\ 0 & 0 & 1 & 0 \end{bmatrix} \begin{bmatrix} x \\ y \\ z \\ 1 \end{bmatrix} \quad \text{(eq. 2)}$$

Next, a photographic image with coordinates (u, v) is acquired from the projection image in the plane z=f. This readout process is subject to a scaling, shear and translation, which can be represented as a 3×3 matrix.
Hence, $$\begin{bmatrix} u \\ v \\ 1 \end{bmatrix} \cong \begin{bmatrix} s_x & k_x & u_0 \\ k_y & s_y & v_0 \\ 0 & 0 & 1 \end{bmatrix} \begin{bmatrix} x_p \\ y_p \\ 1 \end{bmatrix} \quad \text{(eq. 3)}$$

Combining (Eq. 2) and (Eq. 3) yields $$\begin{bmatrix} u \\ v \\ 1 \end{bmatrix} \cong \begin{bmatrix} s_x & k_x & u_0 \\ k_y & s_y & v_0 \\ 0 & 0 & 1 \end{bmatrix} \begin{bmatrix} f & 0 & 0 \\ 0 & f & 0 \\ 0 & 0 & 1 \end{bmatrix} \begin{bmatrix} 1 & 0 & 0 & 0 \\ 0 & 1 & 0 & 0 \\ 0 & 0 & 1 & 0 \end{bmatrix} \begin{bmatrix} x \\ y \\ z \\ 1 \end{bmatrix} \quad \text{(eq. 4)}$$

For technical reasons related to the camera readout mechanism, $k_y$ is usually 0. Multiplying the matrices in Eq. (4) and substituting $s_x \cdot f$, $s_y \cdot f$ and $k_x \cdot f$ by $f_x$, $f_y$ and $\kappa_x$, respectively, yields:

$$\begin{bmatrix} u \\ v \\ 1 \end{bmatrix} \cong \begin{bmatrix} f_x & \kappa_x & u_0 & 0 \\ 0 & f_y & v_0 & 0 \\ 0 & 0 & 1 & 0 \end{bmatrix} \begin{bmatrix} x \\ y \\ z \\ 1 \end{bmatrix} \quad \text{(eq. 5)}$$

The transformation matrix in (Eq. 5) contains five parameters. When these parameters are known, the camera is said to be calibrated internally. The camera is calibrated externally if the six degrees of freedom of I and R are known. Together, the whole calibration process thus requires eleven parameters to be defined. This can be done by indicating a set of corresponding points on respectively the 3D surface and the 2D photograph (FIG. 5). Each such point yields two equations. This means that at least six points are needed to calculate the value of the eleven parameters. In practice, more reference points are recommended in order to improve the accuracy of the solution.

The internal calibration parameters are very sensitive to small errors on the position of the corresponding reference points. As already mentioned, it is therefore recommended to take first a picture of a separate calibration object with accurately known geometry and texture (FIG. 4), to calculate the internal parameters of the camera, and to freeze these settings during the remainder of the photo session. The corresponding reference points on the acquired 3D image and 2D photographic image of (part of) the body (FIG. 5) are subsequently used for the external calibration.

Figure 6:
FIG. 6 represents an iterative improvement of the accuracy by using additional corresponding points on the 2D photograph and the projected surface mesh.
Figure 6:
Figure 6:
Figure 6:

The accuracy of the registration can iteratively be improved by adding corresponding points on the 2D photograph and the projected surface mesh (FIG. 6).

Instead of using a set of corresponding points, registration of the 3D surface with a 2D photograph can also be performed for example based on the optimisation of an objective function that expresses the correspondence between 2D-image-derived features and 3D-shape-based properties (e.g., mutual information).

Figure 8:
FIG. 8 represents a spherical texture map assembled from the photographs in FIG. 3b.

In a further step a 2D texture map is created from the registered 2D photographs. The surface mesh and corresponding texture are used for 3D visualisation. The texture map is then mapped onto the 3D body surface. View-dependent (using a single texture map for fast displaying, e.g., a virtual sphere enclosing the 3D body contour) and view-independent texture mapping (FIG. 8) assume a known relationship between the 3D surface coordinates and the 2D photographic coordinates, as well as a method to calculate the texture values from the colours or gray values in the available photographs.

Figure 1D:
FIG. 1d represents two views of the rendered surface mesh, using a texture map obtained from the set of 2D photographs.
Figure 1D:
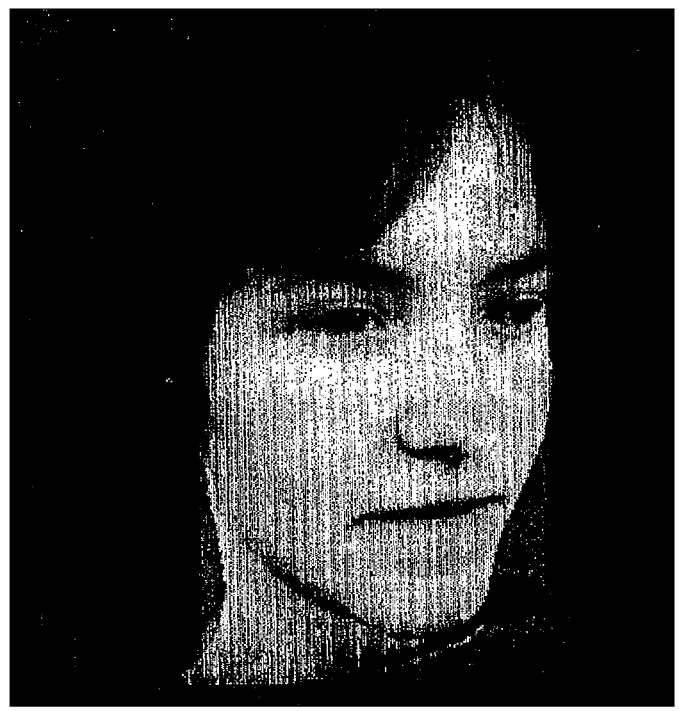
Figure 2D:
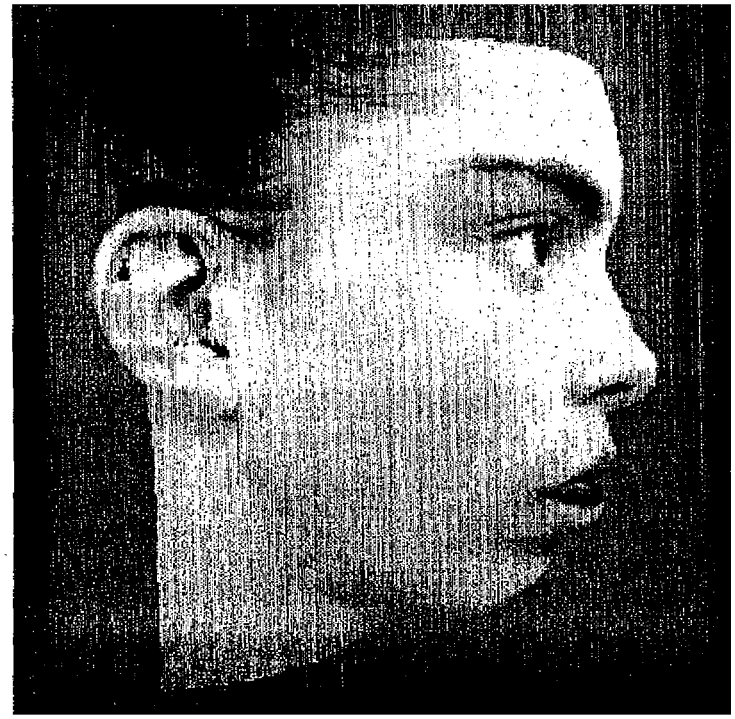
FIG. 2d represents two views of the rendered surface mesh, using a texture map obtained from the set of 2D photographs.
Figure 2D:
Figure 3C:
FIG. 3c offers six views of the rendered surface mesh using a texture map obtained from the set of 2D photographs.
Figure 3C:
Figure 3C:
Figure 3C:
Figure 3C:
Figure 3C:

Once the 2D photographs and 3D surface are matched, the mapping between the 3D surface coordinates and the 2D coordinates in each photograph is known. Each 3D mesh point corresponds to a point in each 2D photograph and its texture value is nonzero if the 3D mesh point is visible in and front facing at least one of the 2D photographs. Hence, for each 2D photograph, a corresponding "visible mesh" is generated by removing the vertices that are invisible from the camera position, together with the triangles they belong to. The texture value can for example be calculated as a normalised weighted combination of the corresponding colour or gray values in the contributing photographs as proposed in the above-mentioned papers by Pighin or by Iwakiri. This weight function should provide a smooth and seamless transition between the photographic patches. For example, in FIGS. 1d, 2d and 3c the weight function $(\theta-\pi/2)^2$ has been used, with $\theta$ the angle between the surface normal and the line from the surface point to the camera position of the photograph.

A 3D patient-specific planning system (e.g., for maxillofacial surgery, breast augmentation, nose correction, etc.), including a soft tissue prediction, is used to simulate the post-operative shape. The soft tissue prediction is used to deform the pre-operative surface mesh of the soft tissue with associated texture map into a predicted post-operative soft tissue mesh with associated remapped texture. The post-operative soft-tissue mesh and corresponding texture map is used for 3D visualisation of the soft tissue.

Several methods exist to animate a 3D body shape. Motion simulation can be based on heuristic rules, physics-based knowledge, or it can be image-derived (e.g., building a statistical deformation model based on a set of images from different expressions or a linear combination of a set of textured face meshes each corresponding to a facial expression, such as joy, anger, sadness). The result can be natural or artificial (e.g., the facial motion of one person can be used to drive the facial motion of another person).

The system and method makes use of a personalised and accurately predicting 3D deformation field for maxillofacial and plastic surgery. As an example, the next paragraph describes a SD planning system for maxillofacial surgery, which yields an accurate personalised 3D deformation field of the face.

Planning a maxillofacial procedure can be subdivided into two separate parts, e.g., the bone-related planning and the soft tissue simulation.

Figure 9:
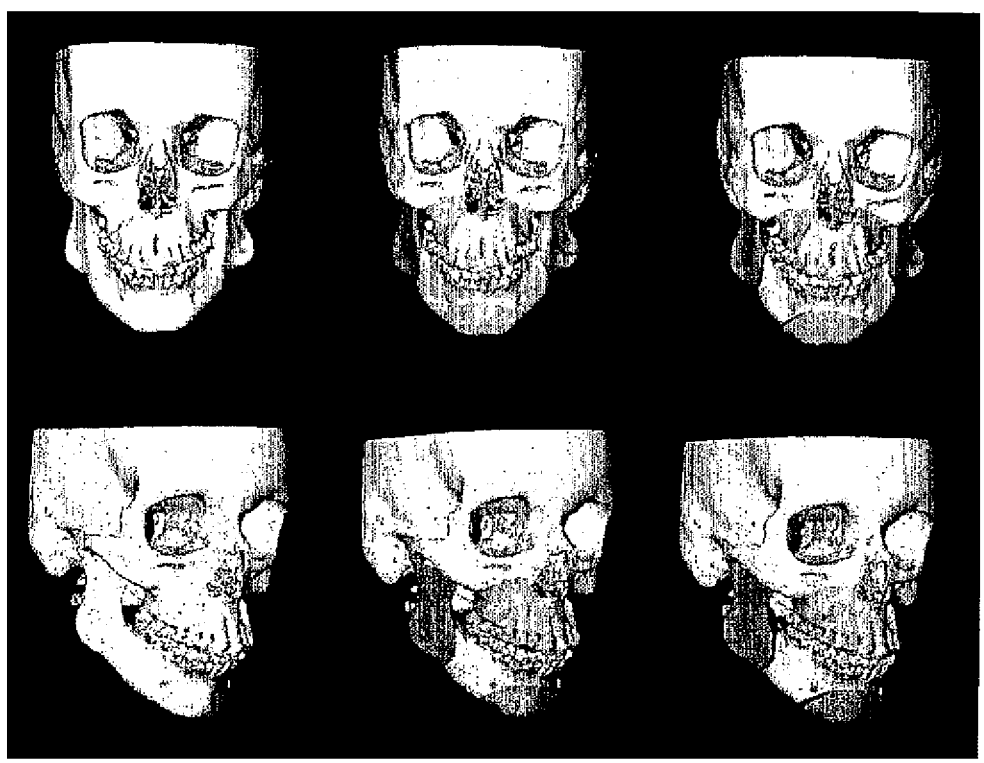
FIG. 9 represents from left to right the initial pre-operative skull. The skull is cut into parts that can be repositioned.
Figure 10:
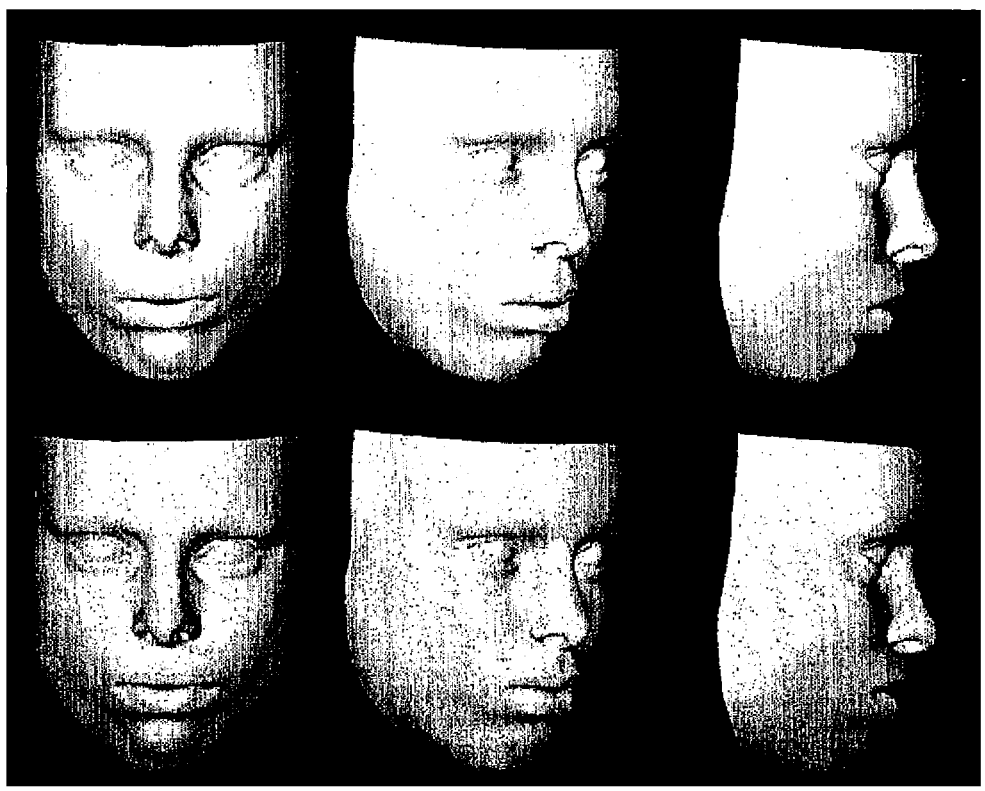
FIG. 10 represents on the top row the pre-operative facial skin surface and on the bottom row the predicted post-operative skin surface.
Figure 11:
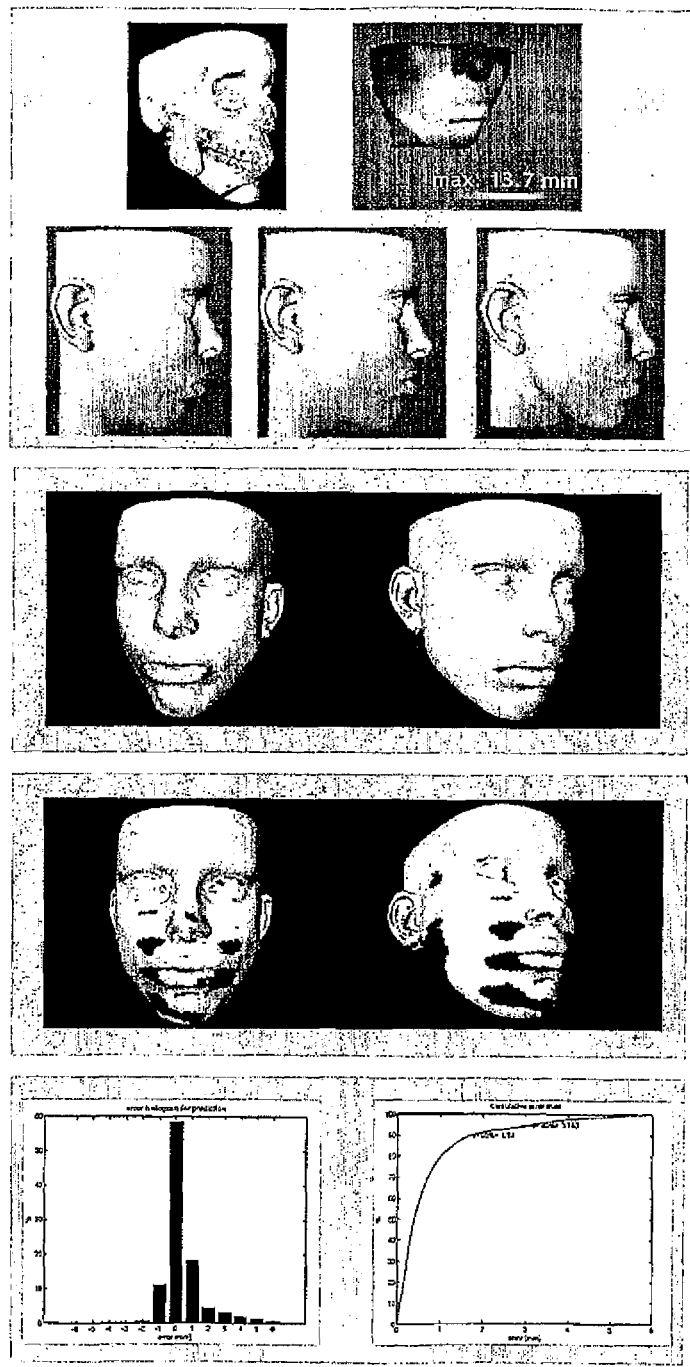
FIG. 11 illustrates the planning system accuracy. Above: bone displacement field (up to 13.7 mm). Middle: the rendered surfaces correspond to positions on the face where the difference between simulated (pre-operative) and real (post-operative) surface are less than 2 mm and 1 mm, respectively. Below: histogram (left) and cumulative histogram (right) of these differences.

The bone-related planner allows the surgeon to reshape the skull in a 3D environment. Reshaping the skull implies cutting the skull into different parts and repositioning each of the different parts (FIG. 9). Starting from a bone related planning, the new facial shape of the patient can be simulated (FIGS. 10). To predict the new facial outlook, a mathematical model is used that is able to accurately simulate the behaviour of the facial tissues. Known models are the finite element model (FEM), the mass-spring model (MSM) and the mass-tensor model (MTM). Together with one of these models, a set of boundary conditions is used, which are generated from the bone-related planning. In 'Very fast soft tissue predictions with mass tensor model for maxillofacial surgery planning systems' (Mollemans et al., Proc Computer Assisted Radiology and Surgery (CARS), 2005) for example, it is assumed that the soft tissue is attached to the bone in a number of locations and that the soft tissue in these points follows the same motion trajectory as the corresponding attaching skull points. The deformation of the remainder of the soft tissue is found by requiring that the total force in each such soft tissue point should be zero or by integrating a motion equation over time. FIG. 11 shows the accuracy of the simulation.

Figure 12:
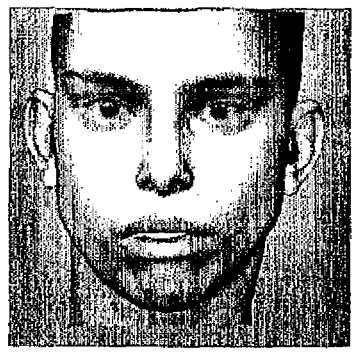
FIG. 12 represents snapshots of the 3D planning system at work, with facility for soft tissue prediction. The face is shown as a 3D rendered texture surface (pre-operative state) and as a 3D rendered textured surface (simulated post-operative state).
Figure 12:
Figure 12:
Figure 12:
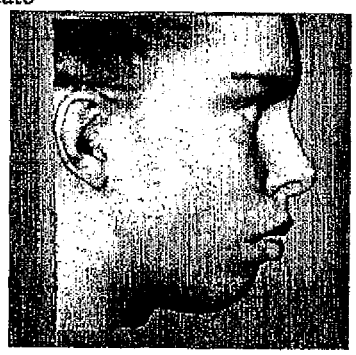
Figure 12:
Figure 12:
Figure 12:
Figure 12:
Figure 13:
FIG. 13 represents a cylindrical texture map assembled from the photographs in FIG. 2b.

FIG. 12 shows a few snapshots of the planning system at work on the same patient as used in FIGS. 9-11. The soft tissue with associated texture moves in real time and simultaneously with the bone displacements. FIG. 13 shows the associated texture map for this patient.

In a further step the 3D pre-operative and post-operative surface meshes are projected onto the pre-operative 2D photographs. The vertices of the pre-operative 3D surface meshes that are visible from the camera viewpoint were previously mapped or projected onto the pre-operative 2D photographs (FIGS. 1a, 2a, 3a) using the registration parameters and matrices previously obtained. For each of these vertices a displacement vector and corresponding vertex in the post-operative 3D surface mesh is known. These corresponding vertices are also projected onto the pre-operative 2D photographs. Since the pre-operative 3D surface mesh is deformed into a post-operative mesh, some vertices that were previously visible, may become invisible now. These vertices are also removed as well as their associated vertex in the pre-operative mesh.

Figure 1C:
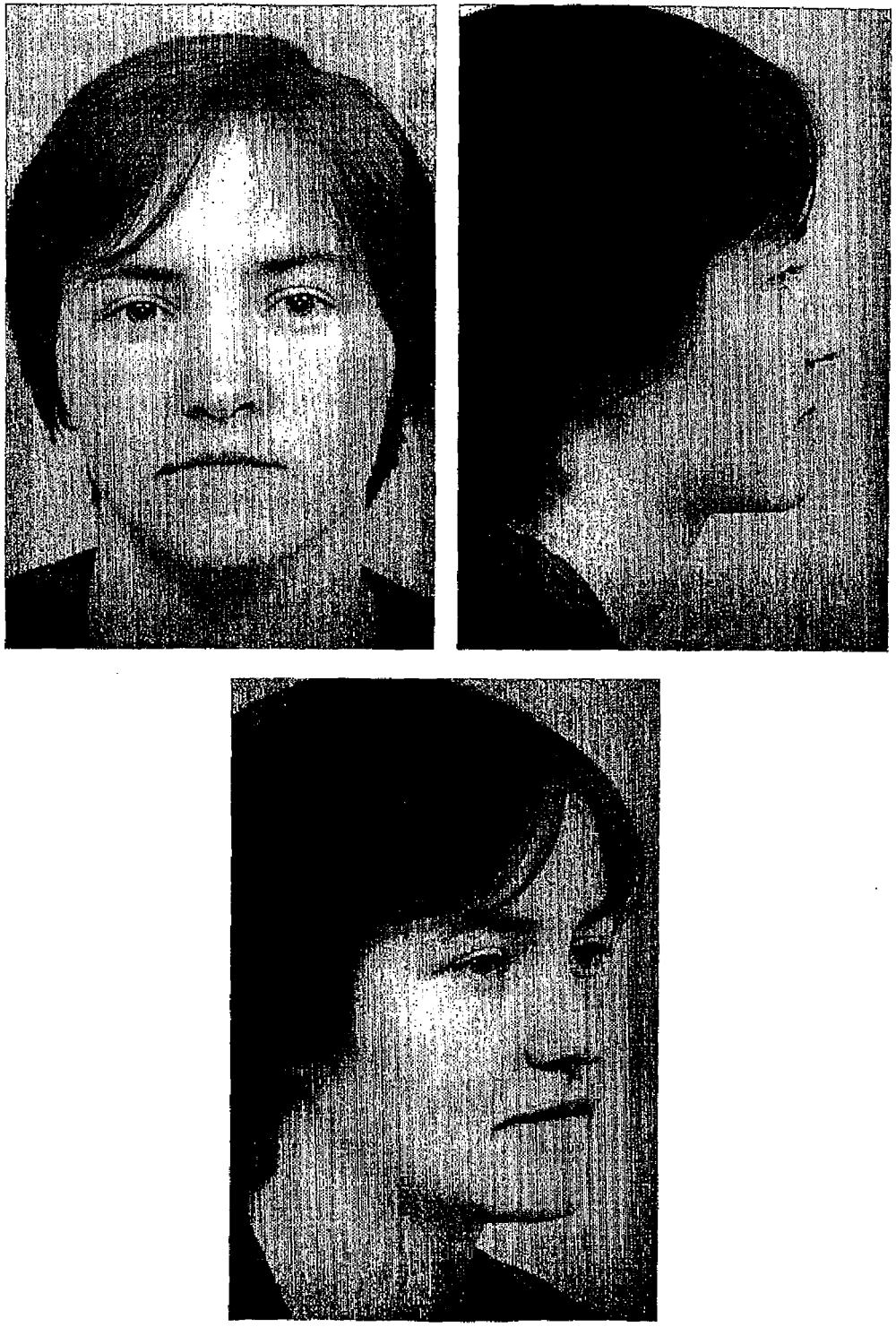
Figure 2C:

The projected deformation field, acquired from the pre-operative and post-operative soft-tissue meshes, is used to geometrically deform the pre-operative 2D photographs and predict the post-operative 2D photographs (FIGS. 1c, 2c).

In computer graphics, pure 2D image processing using a colour/gray value transformation and/or a geometric transformation has been exploited to show (part of) the body under simulated or artificial illumination conditions and for animation by morphing (part of) the body. In these applications, photo-realism is the primary concern. In maxillofacial and plastic surgery, however, the simulated images must accurately predict the post-operative appearance.

Figure 14:
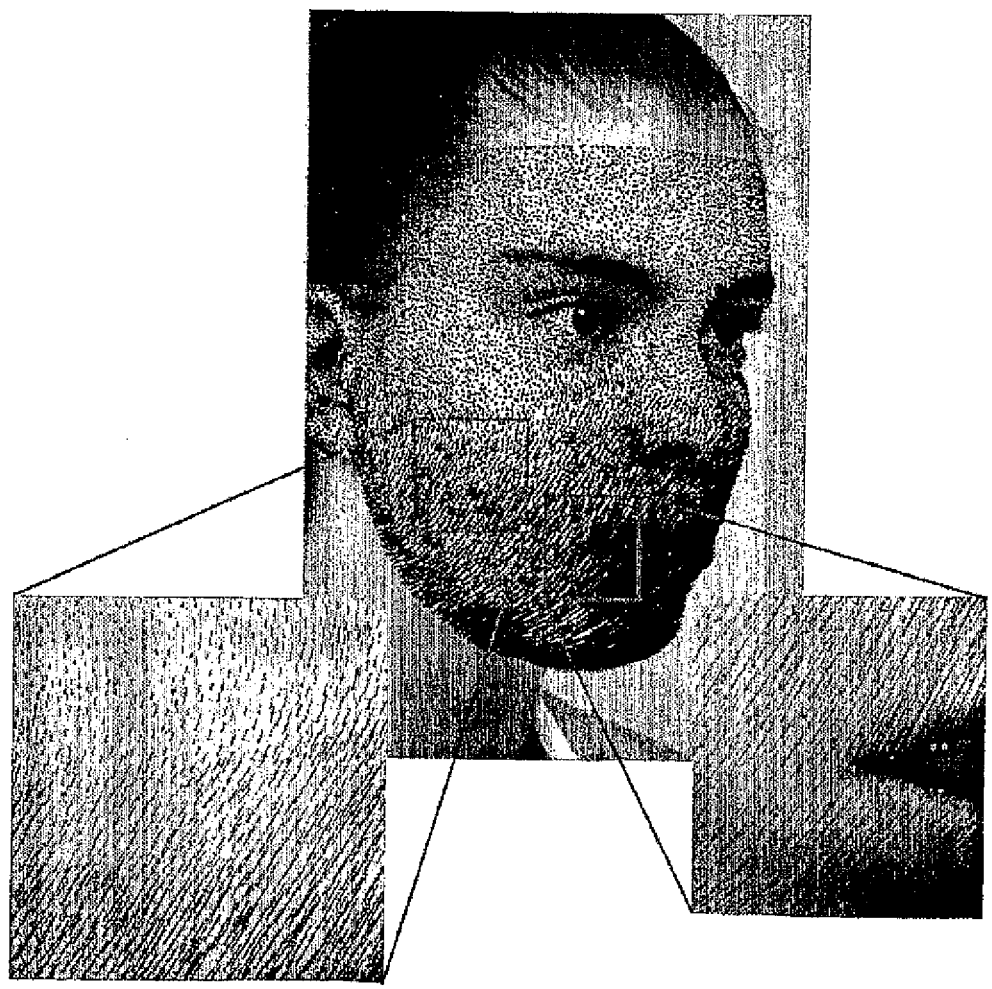
FIG. 14 represents the deformation field (short lines) projected onto the 2D image.
Figure 15:
FIG. 15 represents the displacement field (short lines) and boundary of the dilated region (outer contour). Outside this area, the displacements are zero and the image is not deformed.

A patient-specific 3D deformation model is used to deform the 2D photographs geometrically. From the projected pre-operative and post-operative soft-tissue meshes, the 2D displacement of all the projected mesh vertices in the 2D photograph is known. Hence, the 2D geometric deformation vector is known in a discrete number of points in the 2D photograph (FIG. 14). The displacement in each pixel of the photograph can then be calculated by interpolation between the discrete deformation vectors. Outside the projected mesh, the deformation is in principle zero. However, due to small mismatches between the 2D photograph and the projected pre-operative surface mesh, it may be recommended to slightly extrapolate the deformation field outside the mesh. Mismatches particularly occur if the posture of the (part of) the body is different in the 2D photograph and the 3D surface (e.g., taken in standing and lying position, respectively). FIG. 15 is a typical example. In this case, the contour of an enlarged region can be used as the zero-deformation borderline. Within this region, interpolation of the discrete deformation field can for example be performed using bicubic spline functions.

The above method can also be used in practice without determining a deformation field and using the deformation field to deform the one or more pre-operative 2D photographs. The latter step results in a predicted post-operative 2D photograph. However, 3D visualisation using texture mapping lacks photo-realism (e.g., unnatural texture blending and hair modelling artifacts (particularly when using medical imaging, such as CT for 3D image acquisition) and the texture map mostly needs retouching. The simulated post-operative 2D photograph on the other hand, has intrinsically the same photo-realism as the original pre-operative photograph.

What is claimed is:

1. A method for pre-operatively obtaining a prediction of a post-operative image of at least part of a body, comprising:
    determining a 3D pre-operative model of at least part of a body;
    acquiring a pre-operative 2D photograph of the at least part of the body from one or more viewing positions;
    aligning the 3D pre-operative model with the pre-operative 2D photograph;
    determining a deformation field for deforming the 3D pre-operative model; and
    deriving a predicted 2D post-operative image of a 3D post-operative model of the at least part of the body, the predicted 2D post-operative image being a 2D photograph obtained by deforming the pre-operative 2D photograph using the deformation field according to the alignment.

2. The method as in claim 1, additionally comprising deriving a predicted 3D surface rendering of the 3D post operative model.

3. The method as in claim 2, wherein a plurality of pre-operative 2D photographs is acquired.

4. The method as in claim 1, further comprising generating from the 3D pre-operative model a 3D pre-operative surface mesh of at least the contours of the at least part of the body.

5. The method as in claim 4, wherein deriving the predicted image comprises deriving from the 3D pre-operative surface mesh a prediction of a 3D post-operative surface mesh of at least the contours of the at least part of the body.

6. The method as in claim 5, wherein the prediction of the contours is used in the determination of the deformation field.

7. The method as in claim 1, wherein the 3D pre-operative model is obtained using a 3D image acquisition system.

8. The method as in claim 7, wherein the 3D image acquisition system is a Computerized Tomography system, a Magnetic Resonance Imaging system or a 3D photographic system.

9. The method as in claim 1, wherein the aligning is performed by a set of corresponding points on the 3D pre-operative model and the 2D pre-operative photograph.

10. The method as in claim 1, wherein the aligning is performed by a metric expressing the correspondence between features derived from the pre-operative 2D photograph and features derived from the 3D pre-operative model.

11. The method as in claim 1, further comprising taking a picture of a calibration object.

12. The method as in claim 11, wherein the picture of the calibration object is used for calibrating a camera, the camera being used for acquiring the pre-operative 2D photograph.

13. The method as in claim 3, wherein after the aligning, additionally comprising creating from the aligned pre-operative 2D photographs a texture map for 3D visualization.

14. The method as in claim 1, wherein the 3D pre-operative model comprises a soft tissue description of the at least part of the body.

15. The method as in claim 1, wherein the 3D pre-operative model of the at least part of the body comprises information about the internal structure of the at least part of the body.

16. A surgical planning system for pre-operatively showing a predicted post-operative image of at least part of a body, the system comprising:
    means for determining a 3D pre-operative model of at least part of a body;
    means for aligning the 3D pre-operative model with a 2D pre-operative photograph of the at least part of the body;
    calculation means for determining a deformation field to deform the 3D pre-operative model and for deriving a predicted 2D post-operative image of a 3D post-operative model of the at least part of the body, the predicted 2D post-operative image being a predicted post-operative 2D photograph obtainable by deforming the pre-operative 2D photograph using the deformation field according to the alignment; and
    display means for showing the predicted post-operative image.

17. The surgical planning system as in claim 16, wherein the calculation means additionally derives a predicted post-operative 3D image of the 3D post-operative model.

18. The method as in claim 1, wherein deforming the pre-operative 2D photograph comprises displacing pixels in the pre-operative 2D photograph by a deformation vector based on the deformation field.

19. The system as in claim 16, wherein deforming the pre-operative 2D photograph comprises displacing pixels in the pre-operative 2D photograph by a deformation vector based on the deformation field.

20. The method as in claim 1, wherein the deformation field includes a deformation vector indicative of a displacement between the vertices of a 3D pre-operative surface mesh generated from the 3D pre-operative model and a predicted 3D post-operative surface mesh derived from the 3D pre-operative surface mesh.

21. The method as in claim 20, wherein a displacement of each pixel of the pre-operative 2D photograph is calculated by interpolation between discrete deformation vectors corresponding to a discrete number of points in the pre-operative 2D photograph.

22. The method as in claim 21, wherein the interpolation utilizes bicubic spline functions.

23. The method as in claim 20, additionally comprising extrapolating the deformation field outside the 3D pre-operative surface mesh.

24. The method as in claim 1, wherein acquiring a pre-operative 2D photograph comprises integrally capturing the pre-operative 2D photograph with a camera.

* * * * *